United States Patent [19]

Conley et al.

[11] 4,384,829

[45] May 24, 1983

[54] PUMP AND ACTUATOR MECHANISM

[75] Inventors: Michael G. Conley, El Cerrito; James S. Petrek, Berkeley, both of Calif.

[73] Assignee: Andros Incorporated, Berkeley, Calif.

[21] Appl. No.: 211,210

[22] Filed: Nov. 28, 1980

[51] Int. Cl.$^3$ ............................................. F04B 43/04
[52] U.S. Cl. ........................................ 417/412; 3/1.7; 92/50; 128/1 D; 128/DIG. 3; 310/22; 310/33
[58] Field of Search ............... 417/410, 411, 412, 413, 417/415–417, 472, 478; 128/1 D, DIG. 3; 3/1.7; 310/21, 22, 25, 28, 32, 33; 92/50, 90

[56] References Cited

U.S. PATENT DOCUMENTS

| | | | |
|---|---|---|---|
| 1,893,776 | 1/1933 | Hull | 417/478 |
| 2,816,514 | 12/1957 | Freese | 417/412 |
| 3,263,105 | 7/1966 | Heyek | 310/22 X |
| 3,308,361 | 3/1967 | Nakai et al. | 310/22 X |
| 3,633,217 | 1/1972 | Lance | |
| 3,963,380 | 6/1976 | Thomas et al. | 417/412 X |
| 4,167,046 | 9/1979 | Portner et al. | 417/412 X |

OTHER PUBLICATIONS

Bindels, J. and J. Grigsby, "Considerations and Calculations about the Optimum Solenoid to be used for an Intrathoracic Artificial Heart," Trans. Amer. Soc. Artif. Int. Organs, 7:369, 1961.
Bindels, J., "Theoretical Limits of Efficiency for Solenoids to Drive Artificial Hearts," Trans. Amer. Soc. Artif. Int. Organs, 8:140, 1962.
Freebairn, D., and T. Heggs, "Solenoid Design for a Prosthetic Heart," Trans. Amer. Soc. Artif. Int. Organs, 10:166, 1964.
Fuller, J. W., H. M. Bourland, W. O'Bannon, D. Liotta, C. W. Hall and A. S. Bahler, "A Solenoid Powered Ventricular Bypass Pump," Trans. Amer. Soc. Artif. Int. Organs, 14:352, 1968.
Fuller, J. W. and L. Armijo, "Design Analysis for a Solenoid Blood Pump Actuator," IEEE Trans. Biomed. Eng., 16:184, 1969.
Portner, P. M., J. S. Jassawalla and D. H. LaForge, "An Implantable Controlled Solenoid Energy System for Driving an Artificial Heart," 7th Intersoc. Energy Conv. Eng. Conf. Proc. (1972), p. 784.
Jassawalla, J. S., D. H. LaForge and P. M. Portner, "An Implantable Left Ventricular Assist System Utilizing a Controlled Solenoid Energy Converter," 10th Intersoc. Energy Conv. Eng. Conf. (1975), p. 1466.
Jassawalla, J. S., P. J. Miller and P. M. Portner, "Evolution of an Implantable Pulsed Solenoid Cardiac Assist System," Proc. 29th Ann. Conf. Eng. Med. Biol. (1976), p. 243.
Portner, P. M., P. E. Oyer, J. S. Jassawalla, P. J. Miller, H. Chen, D. H. LaForge and K. W. Skytte, "An Implantable Permanent Left Ventricular Assist System for Man," Trans. Amer. Soc. Artif. Int. Organs, 24, 98 (1978).
Portner, P. M., P. E. Oyer, P. J. Miller, J. S. Jassawalla, A. K. Ream, S. D. Corbin and K. W. Skytte, "Evolution of the Solenoid Actuated Left Ventricular Assist System: Integration with a Pusher-Plate Pump for Intra-Abdominal Implantation in the Calf, " Artif. Organs 2, 402 (1978).
Portner, P. M., P. E. Oyer, J. S. Jassawalla, P. J. Miller, K. W. Skytte, D. H. LaForge, A. K. Ream, S. D. Corbin and M. E. Billingham, "Development and in Vivo Evaluation of the Solenoid Actuated Left Ventricular Assist System," Proc. Annual Contractors Meeting, Devices and Technology Branch, NHLBI, (1978), pp. 73–74.
Portner, P. M., P. E. Oyer, J. S. Jassawalla, P. J. Miller, K. W. Skytte, D. H. LaForge, J. S. Petrek, James Lee, A. K. Ream, M. E. Billingham, "Development and in Vivo Evaluation of the Solenoid Actuated Left Ventricular Assist System," Proc. Annual Contractors Meeting, Device and Technology Branch, NHLBI, (1979), pp. 41–42.

*Primary Examiner*—Edward K. Look
*Attorney, Agent, or Firm*—Fitch, Even, Tabin & Flannery

[57] ABSTRACT

A pump is described in which a flexible enclosure defines a pump chamber and in which the contents of the pump chamber are expelled by movement of a pair of opposed pusher elements engaged with the enclosure. The pusher elements are displaced by at least one pair of beam springs, each of which is pivotally supported at one end and is engaged with one of the pusher elements at the other end. The ends of the beam springs opposite the pusher elements are pivoted by actuation of symmetrical solenoid armatures, causing each of the springs to be stressed. Relief of the spring stress forces the pusher elements toward each other. De-energization of the solenoid armatures permits the beam springs to pivot back to the original position upon filling of the pump chamber.

23 Claims, 6 Drawing Figures

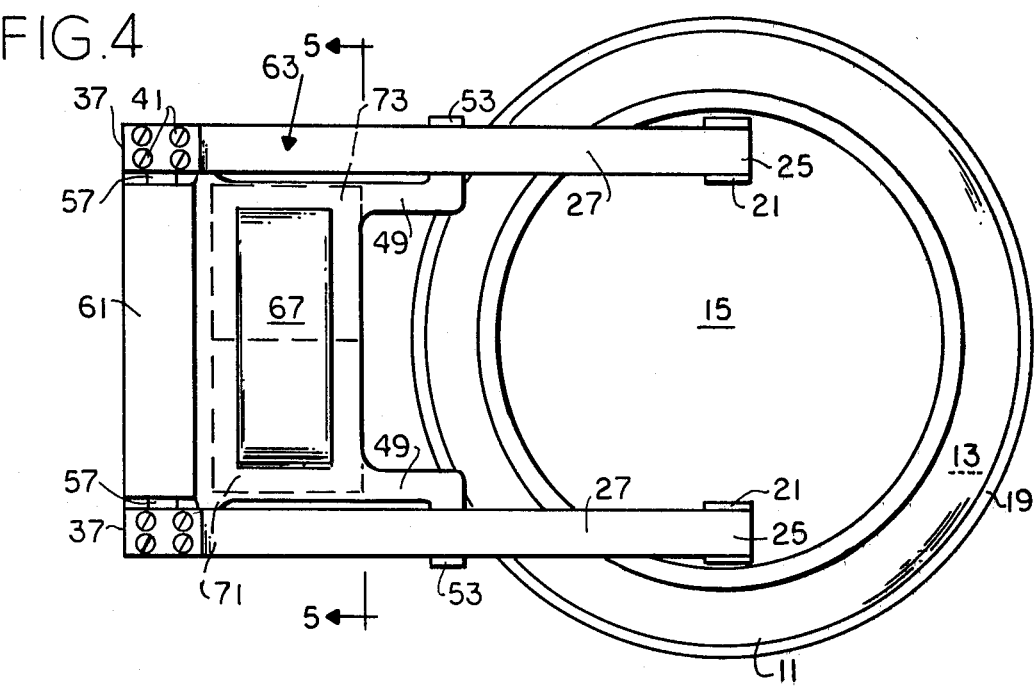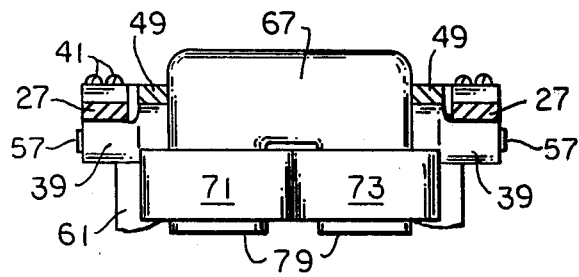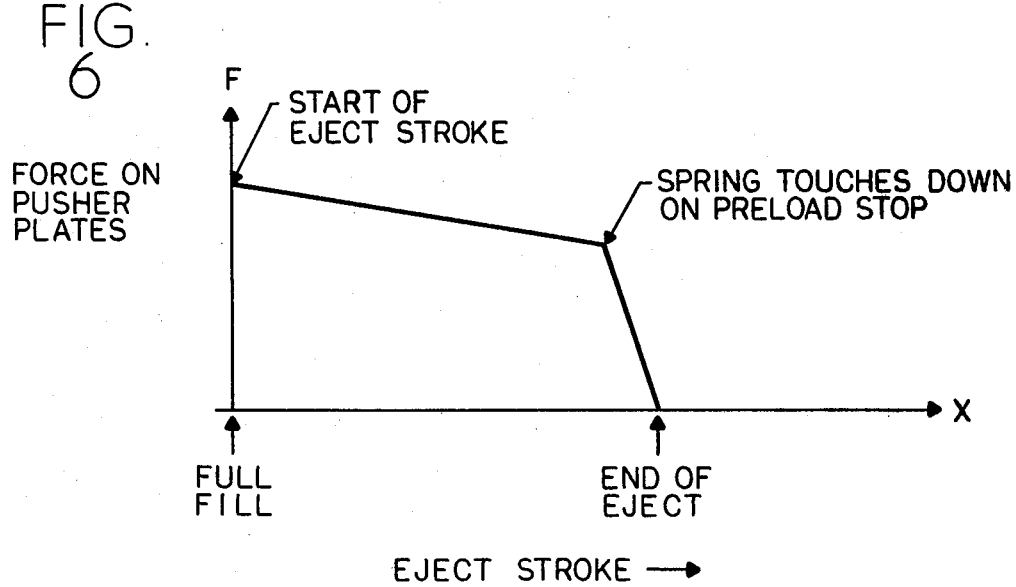

PUMP AND ACTUATOR MECHANISM

This invention relates generally to pumps and the like. More particularly, the invention relates to an improved actuator mechanism for a pump, the pump and actuator mechanism being particularly suited for use as an internally implanted blood pump.

In some instances, it may be advantageous to employ, in a pump, a pair of opposed pusher elements moveable reciprocally from a relatively more displaced first position to a relatively less displaced second position for expelling the contents of the pump chamber. By way of example, a pump of this general type is shown and described in U.S. Pat. No. 4,167,046. This pump is for internal use in humans and animals as a left ventricular assist device. The device is comprised of a unitary pancake shaped deformable sac of flexible resilient blood-compatible material. A pair of oppositely acting plates on each side of the pancake shaped sac are moved toward each other to compress the sac and provide for expelling the contents of the sac. Various advantages accrue from this construction as set forth in the aforementioned patent.

In that patent, the actuator mechanism described includes a pair of arms which are pivotally mounted at one end and which are coupled by suitable linkages to the pusher plates. It is suggested in the patent that these arms be moved by a solenoid actuator such as is available from Andros Incorporated, Berkeley, Calif., under the designation MK19 and MK20.

Actuators of the foregoing type generally include a solenoid which is energized from a storage capacitor in accordance with an internally stored program in a microprocessor. Energization of the solenoid results in the storage of energy in a coil spring or torsion bar. The energy stored in the spring or torsion bar is then transferred through a suitable linkage to the arms which, in turn, displace the pusher plates.

The present invention relates to improvements in the actuator design which represent a technological breakthrough in that very significant savings result in overall size and weight and in the number of required elements. This makes the device much more suitable for implantation, and increases its reliability. Moreover, although described herein in connection with a left ventricular assist device or similar pump, the invention has broader application where its particular operational characteristics are suited to move opposed elements against a resisting force.

More particularly, a general object of the invention is to provide an improved actuator mechanism for moving opposed elements against a resisting force from a relatively more displaced first position to a relatively less displaced second position.

Another and more particular object of the invention is to provide a pump of the type in which a flexible enclosure defines a pump chamber the contents of which are expelled by movement of opposed pusher elements, wherein the pump is provided with an improved actuator mechanism.

A still further object of the invention is to provide an actuator mechanism for moving opposed elements against a resisting force wherein the mechanism is low in size and weight and more simple of construction than other known mechanisms of this type.

Other objects of the invention will become apparent to those skilled in the art from the following description taken in connection with the accompanying drawings wherein:

FIG. 4 is a top view of the pump of FIGS. 1-3;

FIG. 5 is a sectional view taken on the lines 5—5 of FIGS. 3 and 4; and

FIG. 6 is a graph illustrating the force exerted on the pusher plates by one of the beam springs with respect to the ejection stroke.

Very generally, the improved actuator mechanism includes at least one pair of elongated beam springs, each having one end coupled to a respective one of the pusher elements to be displaced. The ends of the beam springs opposite the one ends are supported for pivotal movement about axes extending transversely of the major dimension of the beam springs. Means are provided for pivoting the beam springs about the respective axes from a first position wherein, with the pusher elements relatively far apart, the beam springs are relatively less stressed, to a second position wherein, with the pusher elements relatively further apart, the beam springs are relatively more stressed. Thus, in relieving the stress, the ends of the beam springs coupled to the pusher elements are displaced to move the pusher elements to the second position.

In the preferred embodiment illustrated in FIGS. 1-5, the actuator mechanism is shown used in conjunction with a pump of the type shown and described in the aforementioned U.S. Pat. No. 4,167,046. The pump includes an enclosure 11 defining a pumping chamber 13 which is for the purpose of serving as a left vetricular assist device to be implanted in a human or animal patient. The contents of the pumping chamber 13 are expelled when two pusher plates 15 and 17 are moved toward each other. The pusher plates, being disposed on opposite sides of the enclosure 11 and in contact therewith serve to compress the flexible enclosure and force the contents of the pump chamber out through a suitable outlet duct, not shown. Greater detail of this pump chamber configuration is given in the aforementioned U.S. patent. An annular support 19 surrounds the flexible enclosure 11 to position it with respect to the remaining portions of the pump including the actuator mechanism.

Figure 1:
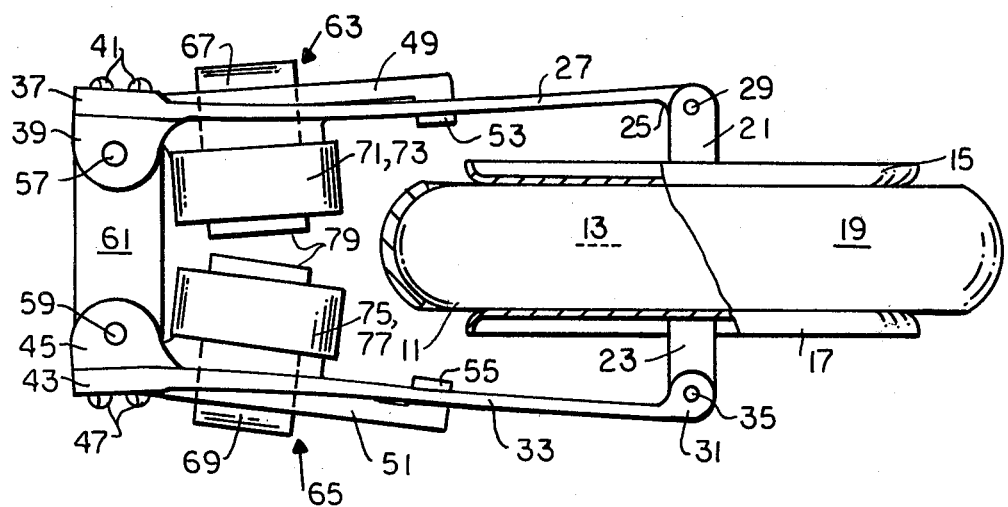
FIG. 1 is a cross-sectional schematic view of a pump constructed in accordance with the invention.
Figure 2:
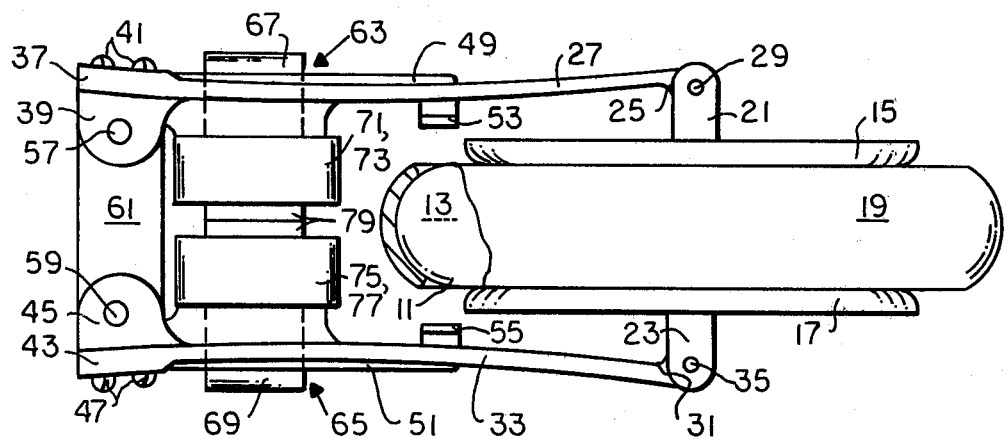
FIG. 2 is a cross-sectional schematic view similar to FIG. 1 illustrating a second condition of the pump.
Figure 3:
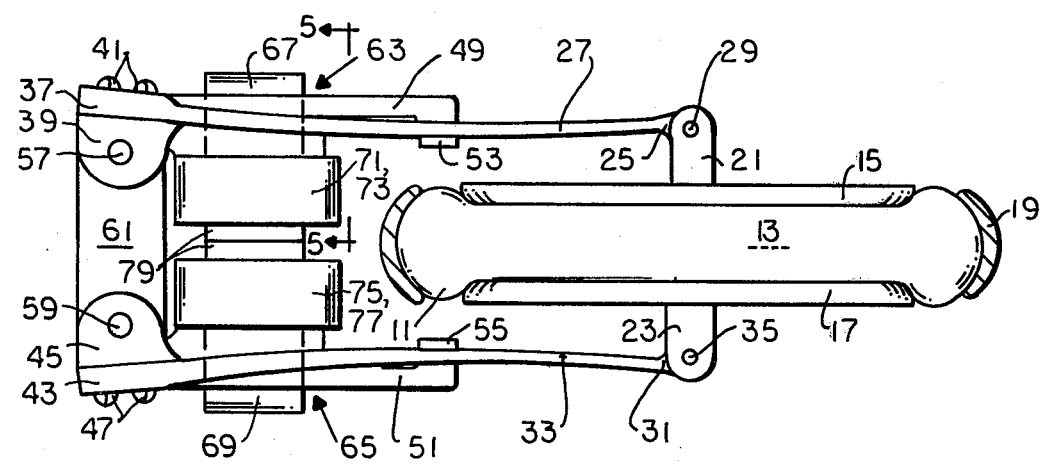
FIG. 3 is a cross-sectional schematic view of the pump of FIG. 1 illustrating a third condition of the pump.

In the illustrated embodiment of the invention, four beam springs are used as shown by comparing FIGS. 1-3 with FIG. 4. However, two beam springs will suffice in some applications and the four springs are used in the illustrated embodiment so the solenoid beams may be of minimal size. A pair of posts 21 and 23, respectively, extends from each of the plates 15 and 17 positioned approximately at the center of the generally circular plates. The posts 21 are pivotally connected to the flanged ends 25 of a pair of beam springs 27 by pins 29. Similarly, the posts 23 are pivotally connected to the flanged ends 31 of a pair of beam springs 33 by pivot pins 35.

The opposite ends of the beam springs 27 from the ends 25 are provided with portions 37 of slightly enlarged cross-section. The sections 37 are riveted to a support 39 by rivets 41 passing through the portions 37 into the support 39. Similarly, the ends of the beams 33 opposite the ends 31 are provided with enlarged thickness portions 43 which are riveted to a support 45 by means of rivets 47.

Each of the supports 39 and 45, respectively, is provided with a pair of arms 49 and 51, respectively, extending therefrom coextensively with the corresponding beam springs 27 and 33. Projections or preload stops 53 are provided on the free ends of the arms 49 projecting under the corresponding one of the beam springs 27. Similar preload stops 55 are provided on the free ends of the arms 51 projecting over the corresponding one of the beam springs 33. For reasons which will be explained subsequently, the mating surfaces of the portions 37 of the beam springs 27 and the support 39 lie in a plane such that the engaging points of the preload stops 53 project beyond that plane and, accordingly, preload the beam springs 27 in bending stress. A similar relationship with the preload stops 55 and the mating surfaces of the support 45 and the portions 43 of the beam springs 33 provides a preload for the beam springs 33. The result is that each of the beam springs 27 and 33 is always stressed in bending by a minimum amount provided by the preload of the preload stops 53 and 55.

Each of the supports 39 and 45 is mounted for pivotal movement about an axis through a pivot pin 57 and 59, respectively. Thus, as the support 39 pivots on the pin 57, so likewise do the sections 37 of the beam springs 27 move pivotally about the axis. Similarly, as the support 45 pivots on the axis of the pin 59, so likewise the ends 43 of the beam springs 33 pivot about the axis of the pin 59 with the support 45. Each of the pins 57 and 59 is supported in a frame 61 which comprises a portion of the general frame (not shown) of the pump which includes the enclosure support 19.

For the purpose of pivoting the beam springs about the axes of the pins 57 and 59, solenoid means are provided. The solenoid means include a pair of solenoid armatures 63 and 65 mounted, respectively, to the supports 39 and 45. The solenoid armature 63 includes a C-shaped core 67, the free ends of which extend through mating openings in the support 49. Similarly, the solenoid armature 65 includes a C-shaped core 69, the free ends of which extend through mating openings in the support 45. The C of the core 67 faces the open side of the C of the core 69 and the free ends are aligned. Each leg of the C-shaped core 67 is surrounded by a coil 71 and 73. Similarly, each leg of the C-shaped core 69 is surrounded by a coil 75 and 77, respectively. Energization of the coils 71, 73, 75, and 77, by suitable control means, not shown, causes the ends of the solenoid cores to be attracted toward each other. To prevent excessive wear, the ends of the solenoid cores are provided with wear pads 79 of suitable material.

The operation of the actuator mechanism and pump may be observed sequentially in FIGS. 1-3. FIG. 1 illustrates the apparatus in a condition in which the pump chamber 13 is full and the solenoid armatures 63 and 65 are unenergized. In this condition, the arms 49 and 51 are swung open to their widest condition as are the beam springs 27 and 33. In this condition, a preload bias is provided to the springs by the preload stops 53 and 55.

The ejection stroke is begun when the storage capacitor, not shown, energizes the solenoid coils 71, 73, 75, and 77. When energized, the armature 63 and 65 are drawn toward each other, moving the arms 49 and 51 to the position shown in FIG. 2. In this position, the inertia of the filled pump chamber 13 and compressible sac 11 retain the ends 25 and 31 of the beam springs 27 and 23 essentially in the same position as in FIG. 1. The preload stops 53 and 55 are moved away from the springs, however, thereby causing the springs to be stressed to a more loaded condition in which they contain greater stored energy.

After closure to the position of FIG. 2, the solenoid means are held there by a relatively small latching current. If additional holding force is needed, a small permanent magnet may be used. The force of the latter may be overcome when necessary by a small reverse current in the solenoid coils.

From the condition in FIG. 2, the natural tendency for the beam springs 27 and 33 to relieve the stressed condition results in the plates 15 and 17 being moved toward each other, thus expelling the contents in the pump chamber 13. At the end of the pump stroke, shown in FIG. 3, the beam springs have returned to their less stressed condition abutting the preload stops 53 and 55. Once this has occurred, the solenoid coils are de-energized or unlatched.

The apparatus is returned to the condition shown in FIG. 1 as the result of the cardiac systole. The solenoid gap thus increases as the supports 39 and 45 pivot about the pivot pins 57 and 59, respectively, as the plates 15 and 17 push out the ends 25 and 31 of the springs 27 and 33. A suitable detector, not shown, is provided to determine the time at which the rate of pump fill drops below a preselected threshold. At this point, a microprocessor, not shown, is programmed to resume the ventricular assist pumping function.

Referring now to FIG. 6, the characteristics of the device may be observed in connection with the relationship between the force on the pusher plates 15 and 17 versus the ejection or expelling stroke distance. The nearly horizontal portion of the curve as the normal characteristic of stress relief in the beam spring. A spring with a relatively low spring constant is selected so that this portion of the curve is as horizontal as possible. It may be seen that at the furthest left-hand edge of the plot, the ejection stroke begins after filling. Ejection proceeds until the springs engage the preload stops, at which time the ejection stroke terminates as shown. The energy retained in the spring by the preloading thus is to the right of the termination of the curve in FIG. 6.

As a result of the foregoing construction, a number of significant advantages accrue. Mechanical simplicity is achieved because the preloaded springs deliver the desired output force profile without the need for motion amplification linkage. Thus, the system has few moving parts, few bearings, and is more compact, more efficient and more reliable than prior art designs. Since the beam springs act directly on the pump pusher plates, no output arms are required, again producing a simpler, lighter system.

Because of the low spring constant used to produce a relatively flat output force profile (FIG. 6), peak spring force in the preloaded spring is much lower than with a linear (non-preloaded) spring, storing an equal amount of energy. As a result, peak loads on the spring, frame and bearings are half that of prior art designs, yielding a reduction in size and mass of most components, and an increase in bearing life and reliability. Moreover, the beam spring has an inherently simple geometry. It has predictable spring characteristics, can be designed with minimal stress concentration factors, and is easy to fabricate. Its simple shape allows a bolted, rather than welded, assembly, facilitating system development and optimization. In addition, because the beam spring is loaded in bending (as opposed to helical compression springs and torsion bars, where the material is loaded in shear), the endurance strength of the spring material is higher, and the spring is less sensitive to surface finish than in prior art designs. Finally, the preloaded spring design results in reduced stress amplitude at the area of highest stress level. This allows a conservative spring design with a high safety factor.

Due to the spring force profile, solenoid closure may be relatively slow. This permits the implementation of a real-time energy servo. Solenoid energy can be adjusted during the final stages of closure, assuring perfect energy matching every beat. This results in quiet operation and optimum efficiency.

It may be seen, therefore, that the invention provides an improved pump system and actuator therefor which are of minimal size and weight, use few parts, and are highly reliable. Various modifications of the invention in addition to those shown and described herein will become apparent to those skilled in the art from the foregoing description and accompanying drawings. Such modifications are intended to fall within the scope of the appended claims.

What is claimed is:

1. A pump comprising a flexible enclosure defining a pump chamber, a pair of opposed pusher elements engaged with said enclosure and being movable reciprocally from a relatively more displaced first position to a relatively less displaced second position for expelling the contents of the pump chamber, an actuator mechanism for moving said pusher elements, said actuator mechanism comprising at least one pair of elongated beam springs, each having one end coupled to a respective one of said pusher elements, means supporting the ends of said beam springs opposite said one ends for pivotal movement about axes extending transversely of the major dimension of said beam springs, said supporting means including means for preloading each of said beam springs in a first position wherein, with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position.

2. A pump according to claim 1 employing two such pairs of beam springs.

3. A pump according to claim 1 wherein said axes about which said beam springs are supported for pivotal movement are substantially parallel.

4. A pump according to claim 1 wherein said supporting means comprise a pair of supports, each pivotal on a respective one of said axes, each of said beam springs being rigidly mounted at the end thereof opposite said one end to a respective one of said supports, and wherein said pivoting means operate to pivot said supports.

5. A pump according to claim 4 wherein each of said supports includes an arm portion extending therefrom along the corresponding one of said beam springs to which said support is attached, said arm portion having a projection at its free end engageable with said one beam spring at a position intermediate its ends to preload said one beam spring.

6. A pump according to claim 4 wherein said pivoting means include a pair of symmetrical solenoid armatures, each connected to a respective one of said supports.

7. A pump according to claim 1 wherein said pivoting means comprise solenoid means.

8. A pump according to claim 7 wherein said solenoid means comprise a pair of symmetrically moveable armatures, each being mechanically coupled to a respective one of said beam springs.

9. In a pump having a pair of opposed pusher elements movable reciprocally from a relatively more displaced first position to a relatively less displaced second position for expelling the contents of a pump chamber, an actuator mechanism for moving said pusher elements, comprising at least one pair of elongated beam springs, each having one end coupled to a respective one of said pusher elements, means supporting the ends of said beam springs opposite said one ends for pivotal movement about axes extending transversely of the major dimension of said beam springs, said supporting means including means for preloading each of said beam springs in a first position wherein with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position.

10. An actuator mechanism according to claim 9 employing two such pairs of beam springs.

11. An actuator mechanism according to claim 9 wherein said axes about which said beam springs are supported for pivotal movement are substantially parallel.

12. An actuator mechanism according to claim 9 wherein said supporting means comprise a pair of supports, each pivotal on a respective one of said axes, each of said beam springs being rigidly mounted at the end thereof opposite said one end to a respective one of said supports, and wherein said pivoting means operate to pivot said supports.

13. An actuator mechanism according to claim 12 wherein each of said supports includes an arm portion extending therefrom along the corresponding one of said beam springs to which said support is attached, said arm portion having a projection at its free end engageable with said one beam spring at a position intermediate its ends to preload said one beam spring.

14. An actuator mechanism according to claim 12 wherein said pivoting means include a pair of symmetrical solenoid armatures, each connected to a respective one of said supports.

15. An actuator mechanism according to claim 9 wherein said pivoting means comprise solenoid means.

16. An actuator mechanism according to claim 15 wherein said solenoid means comprise a pair of symmetrically movable armatures, each being mechanically coupled to a respective one of said beam springs.

17. An actuator mechanism for moving opposed pusher elements against a resisting force from a relatively more displaced first position to a relatively less displaced second position, comprising, at least one pair of elongated beam springs, each having one end coupled to a respective one of said pusher elements, means supporting the ends of said beam springs opposite said one ends for pivotal movement about axes extending transversely of the major dimension of said beam springs, said supporting means including means for preloading each of said beam springs in a first position wherein with said pusher elements in said first position, said beam springs are relatively less stressed, and means for pivoting said beam springs about said axes from said first position to a second position wherein, with said pusher elements in said first position, said beam springs are relatively more stressed, whereby in relieving said stress, said one ends of said beam springs are displaced to move said pusher elements to said second position.

18. An actuator mechanism according to claim 17 wherein said axes about which said beam springs are supported for pivotal movement are substantially parallel.

19. An actuator mechanism according to claim 18 wherein said pivoting means include a pair of symmetrical solenoid armatures, each connected to a respective one of said supports.

20. An actuator mechanism according to claim 15 wherein said supporting means comprise a pair of supports, each pivotal on a respective one of said axes, each of said beam springs being rigidly mounted at the end thereof opposite said one end to a respective one of said supports, and wherein said pivoting means operate to pivot said supports.

21. An actuator mechanism according to claim 20 wherein each of said supports includes an arm portion extending therefrom along the corresponding one of said beam springs to which said support is attached, said arm portion having a projection at its free end engageable with said one beam spring at a position intermediate its ends to preload said one beam spring.

22. An actuator mechanism according to claim 21 wherein said solenoid means comprise a pair of symmetrically movable armatures, each being mechanically coupled to a respective one of said beam springs.

23. An actuator mechanism according to claim 17 wherein said pivoting means comprise solenoid means.

* * * * *

UNITED STATES PATENT AND TRADEMARK OFFICE
CERTIFICATE OF CORRECTION

PATENT NO. : 4,384,829

DATED : May 24, 1983

INVENTOR(S) : Conley, *et al.*

It is certified that error appears in the above-identified patent and that said Letters Patent is hereby corrected as shown below:

Column 1, between lines 8 and 9 insert --The governmnet has a non-exclusive, non-transferrable, irrevocable, paid-up license to practice or have practiced for or on behalf of the United States, the subject invention--.

Signed and Sealed this

Fifteenth Day of November, 1994

Attest:

BRUCE LEHMAN

*Attesting Officer*     *Commissioner of Patents and Trademarks*

UNITED STATES PATENT AND TRADEMARK OFFICE
CERTIFICATE OF CORRECTION

PATENT NO. : 4,384,829
DATED : May 24, 1983
INVENTOR(S) : Conley, *et al.*

It is certified that error appears in the above-indentified patent and that said Letters Patent is hereby corrected as shown below:

Delete the language added by the Certificate of Correction issued November 15, 1994. As the first two sentences of Column 1, insert —This invention was made under NO 1-HV-02908 awarded by Public Health Service/National Institutes of Health; National Heart, Lung and Blood Institute. The government has certain rights—.

Signed and Sealed this

Twentieth Day of June, 1995

Attest:

BRUCE LEHMAN

*Attesting Officer*                *Commissioner of Patents and Trademarks*